United States Patent [19]

Stahl et al.

[11] 4,400,260
[45] Aug. 23, 1983

[54] SHIELDED, HEATED ELECTROCHEMICAL GAS SENSOR

[75] Inventors: Roland Stahl, Freiberg; Hans-Martin Wiedenmann, Stuttgart, both of Fed. Rep. of Germany

[73] Assignee: Robert Bosch GmbH, Stuttgart, Fed. Rep. of Germany

[21] Appl. No.: 367,276

[22] Filed: Apr. 12, 1982

[30] Foreign Application Priority Data

May 21, 1981 [DE] Fed. Rep. of Germany ....... 3120159

[51] Int. Cl.³ .............................................. G01N 27/46
[52] U.S. Cl. .................... 204/426; 204/412; 204/425; 204/427; 204/429
[58] Field of Search ............................... 204/15, 195 S

[56] References Cited

U.S. PATENT DOCUMENTS

| | | | |
|---|---|---|---|
| 3,978,006 | 8/1976 | Topp et al. | 204/195 S |
| 4,219,399 | 8/1980 | Gruner et al. | 204/195 S |
| 4,282,080 | 8/1981 | Muller et al. | 204/195 S |
| 4,283,261 | 8/1981 | Maurer et al. | 204/195 S |
| 4,294,679 | 10/1981 | Maurer et al. | 204/195 S |
| 4,294,697 | 10/1981 | Sawa et al. | 210/221 |
| 4,300,990 | 11/1981 | Maurer | 204/195 S |

FOREIGN PATENT DOCUMENTS

| | | |
|---|---|---|
| 3035608 | 3/1982 | Fed. Rep. of Germany . |
| 667471 | 3/1952 | United Kingdom ........... 204/195 G |

*Primary Examiner*—T. Tung

*Attorney, Agent, or Firm*—Frishauf, Holtz, Goodman & Woodward

[57] ABSTRACT

To extend temperature range of solid electrolyte ion conductive-type gas sensors, particularly for the exhaust gases from internal combustion engines, and to prevent leakage currents between a heater element and the solid electrolyte body at temperatures just above the response temperature of the sensor, but below its normal operating temperatures, that is, even in the range of between 250° C. to 400° C., a layer-like shielding electrode (18,29) is provided, positioned between the solid electrolyte body (11,25) and the insulating layer (17,31). The shielding electrode is galvanically connected to the return line (21,33) of the heating element. In accordance with one embodiment, the shielding electrode and one of the operating electrodes, for example, the sensing electrode (29), can be the same metallic film or element applied to the sensor, with an additional electrical insulation layer (32) interposed in the region between the film electrode (29) and the solid electrolyte body (25), the heater element (16,30) being positioned with the interposition of the electrical insulating layer over the film electrode in that region. Preferably, the width of the respective insulating layers decreases in a direction away from solid electrolyte body.

The system is applicable both to potentiometric, as well as polarographic-type sensors, of, selectively, closed tubular or plate-like construction, with electrodes exposed either to a reference gas or having, respectively, different catalytic activity.

4 Claims, 5 Drawing Figures

SHIELDED, HEATED ELECTROCHEMICAL GAS SENSOR

REFERENCE TO RELATED PATENT AND PUBLICATIONS

U.S. Pat. No. 4,300,990, Maurer et al.
U.S. Pat. No. 4,294,679, Maurer et al.
U.S. Pat. No. 4,283,261, Maurer et al.
U.S. Pat. No. 4,219,399, Gruner et al.
U.S. Pat. No. 3,978,006, Topp et al.
DE-OS 30 35 608, Linder et al.

The present invention relates to an electrochemical sensor, and more particularly to a sensor to determine the oxygen content in the exhaust gases from combustion processes, especially exhaust gases from internal combustion engines, for example of the automotive type.

BACKGROUND

Electrochemical sensors, for example, of the type described in the referenced U.S. Pat. No. 4,300,990, Maurer et al., assigned to the assignee of the present application, describes a sensor which has an electrical insulating layer between a layer-like resistance heating element and a solid electrolyte. At low operating temperatures, that is, in temperatures in the region between for example about 250° to 400° C., the layer-like insulation between the resistance heater and the solid electrolyte may have insufficient insulation resistance. Due to this low insulation resistance, leakage currents may arise between the heater element and the electrodes. These leakage currents tend to adulterate the sensing signals derived from the electrodes, that is, by superimposing erroneous voltages thereon. If the sensing signal is used to control the fuel-air ratio of an internal combustion engine, the control may react to this thus falsified sensing signal and may cause erroneous control of the engine. The problem does not arise in the normal working temperature range of the sensor which is above 400° C., since the resistance relationship between solid electrolyte, and the insulation then will be sufficient.

The sensor can be constructed in the form of plates, as described in the referenced Maurer et al U.S. Pat. No. 4,300,990, or may be tubular, for example as described in German Patent Disclosure Document DE-OS 30 35 608. The electrodes may be located on the same side of the solid electrolyte, or on different sides. The sensors may operate in the potentiometric mode, that is, similar to a cell, or in the polarographic, or limit current mode, described, for example, in U.S. Pat. No. 4,294,679. They may operate with reference to a gas of known oxygen content, for example air, in which one electrode is exposed to the reference substance; or it may operate with both electrodes being exposed to the gas to be analyzed, in which, then, the electrodes will have different properties with respect to their electrochemical action, or characteristics, see, for example, the referenced patent 4,294,679.

The sensing elements themselves, whether plate-like or tubular, can be retained in a metal housing, and various constructions may be used; one such construction is shown, for example, in U.S. Pat. No. 4,283,261.

THE INVENTION

It is an object to improve electrochemical sensors so that the operating temperature range thereof is increased, to provide suitable output signals, not only in the high temperature regions, but also in substantially lower temperature regions, in which the output signals are unadulterated by extraneous signals, and in which the requirements for insulation would not place a loading on the sensing element to such an extent that it may be damaged thereby.

Briefly, a shielding electrode is placed between the solid electrolyte and the insulation layer thereover. The shielding electrode is electrically connected with the return line of the heating element, or heating layer. A second electrical insulation layer may be located between the shielding electrode and the solid electrolyte body as such.

In accordance with the feature of the invention, the shielding electrode, while carrying out shielding functions with respect to the heater element as such, may form one of the sensing electrodes of the sensor.

The sensor has the advantage that it is operable not only in high temperature ranges, that is, above 400° C., but is equally operable in lower working temperature ranges, that is, from 250° C. upwardly, and provides output measuring signals which are not affected by voltages derived from the heater unit, while permitting use of insulation which is reasonable and thus does not damage the solid electrolyte, which is highly stressed. Use of an additional electrical insulation layer between the solid electrolyte and the shielding electrode has the advantage that the shielding electrode and one of the electrode layers of the sensor can be constructed as a single continuous layer, connected with the return line of the heater element, or heater connection.

DRAWINGS

Figure 4:
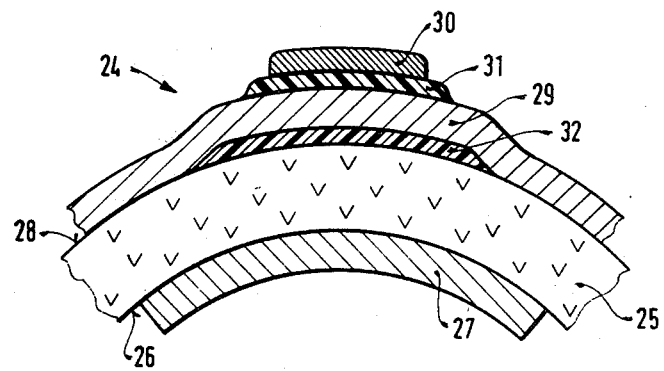
Figure 5:
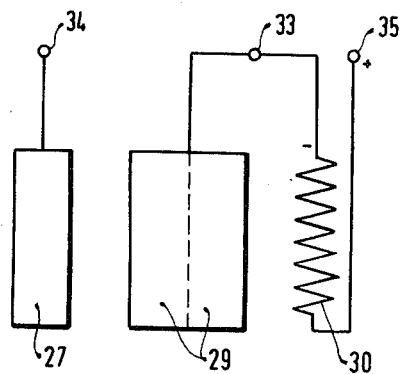

FIG. 4 is a greatly enlarged fragmentary cross-section through a tubular sensor element in which an inner electrode is exposed to a reference substance of known oxygen concentration, for example ambient air; and FIG. 5 illustrates the electrical circuit connection with reference to the reference, measuring and shielding or protective electrode, as well as the heater of the sensor element of FIG. 4.

Figure 1:
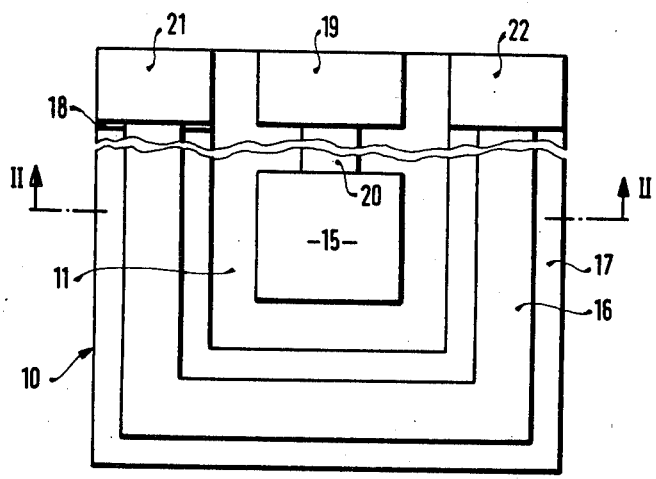
FIG. 1 is a schematic top view of a plate-like sensor, to a greatly enlarged scale, in which the measuring electrode and the reference electrode are exposed to the test or sample gas.
Figure 2:
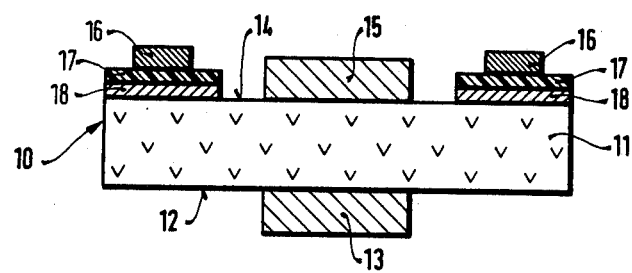
FIG. 2 is a cross-section through the sensor of FIG. 1 taken along line II—II of FIG. 1.

The sensor illustrated in FIGS. 1 and 2 is secured in a housing which, for example, may be of the form described in the referenced patent 4,283,261. Since this construction is known, it need not be further described. The sensor element 10 is utilized to determine the oxygen content in gases, particularly in the combustion exhaust gases derived from internal combustion engines, and includes a plate-like solid electrolyte body 11, having a first major surface 12 on which a reference electrode 13 is applied in accordance with any known and suitable process. The second major surface 14 of the solid electrolyte 11 has a measuring or sensing electrode 15 applied thereon, in accordance with any suitable and well-known process. A layer-like resistance heater 16 surrounds the measuring electrode 15 on the second surface 14. For a detailed description, the referenced Maurer et al. patent 4,300,990 is referred to. The layer-like resistance heating element 16 is located on an electrical insulation layer 17 which is slightly wider than the track of the resistance heating element 16.

In accordance with the invention, the resistance heating element 16, or, rather, the layer of electrical insulation 17 is separated from the surface 14 of the solid electrolyte body 10 by a layer-like protecting or shielding electrode 18. The measuring principle of the sensor is potentiometric; the solid electrolyte 11 may be made of stabilized zirconium dioxide which, above 250° C., has a good conductivity for oxygen ions. The solid electrolyte 11 is about 8 mm wide, 6 cm long, and about 0.8 mm thick. It forms the carrier of the sensor element 10, that is, it is self-supporting.

The measuring electrode 15 applied on the second solid electrolyte surface 14 is placed thereon, for example, by printing, rolling-on or a similar process, and is made of a porous layer of a platinum metal of about 7 $\mu$m thickness. The connecting region 19 is connected with the electrode 15 over a conductive track 20. The connecting region 19 and the conductive track 20 may also be made of a platinum metal and applied by a known process, for example printing on the solid electrolyte plate 11.

The second major surface 12 has a reference electrode 13 applied thereto which is made and applied in accordance with the known process, for example by rolling-on or printing. It is made of a metal which is catalytically less active than that of the measuring electrode 15, for example made of gold, of approximately 7 $\mu$m thickness. The reference electrode 13 is connected over a conductive track—not further identified in the drawings—with a terminal region similar to terminal region 19 (not shown) at the terminal end portion of the sensor element 10.

Both electrodes 13 and 15 are exposed to the gas to be measured and, above about 250° C., act as an electro-chemical cell which provides a useful output signal in the form of a sharp voltage jump if the gas to which it is exposed changes between reducing an oxidizing state, that is, exhibits the voltage jump at about stoichiometric conditions.

In accordance with the invention, the protective or shielding electrode 18 is located in the generally U-shaped marginal regions of the solid electrolyte plate 20, made, for example, of a platinum metal, for example about 8 $\mu$m thick. Additionally, it may contain ceramic components such as aluminum oxide or magnesium spinel, and is positioned at a distance from the measuring electrode 15. The protective electrode 18 is applied in accordance with any known method, such as printing, vapor deposition or the like, on the solid electrolyte plate 11. An electrically insulating layer 17 is then applied over the protective electrode 18, for example made of aluminum oxide and about 60 $\mu$m thick. The electrical insulation layer 17 covers the protective electrode 18, except for a terminal region 21 at the terminal end portion of the solid electrolyte plate 11. The protective electrode terminal region 21 also forms the connecting region for the return line of the resistance heating element 16. The resistance heating element 16 is formed by a layer of platinum or platinum metal of about 20 $\mu$m thickness, and which may also contain some ceramic components. Preferably, it is somewhat narrower than the electrical insulation layer 17. The connecting region 22 for the positive terminal of the resistance heater 16 is connected to the right leg of the U-shaped resistance heating element 16. The resistance heating element 16 may have various path configurations, as described in the referenced Maurer et al patent 4,300,990. For example, it may be meander-shaped, zigzag, or the like, and can be applied by any known process, such as printing or the like, on the electrical insulation layer 17.

The electrodes 13 and 15 and, preferably, also the resistance heater element 16, are preferably covered by a porous protective layer, as known; the porous protective layer is not illustrated in the drawings for clarity thereof.

Figure 3:
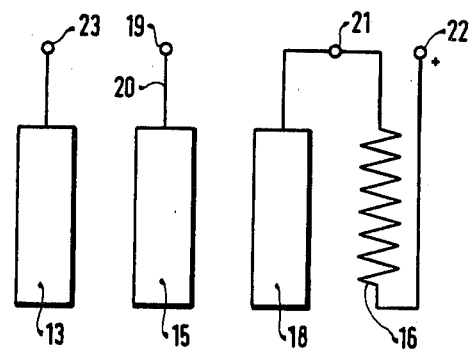
FIG. 3 illustrates, schematically, the electrical connection and the arrangement with respect to reference electrode, sensing electrode and protective electrode, as well as the heater element of the system of FIGS. 1 and 2.

The electrical circuit is shown in FIG. 3. The reference electrode 13 is connected to a terminal connection 23 at the terminal end portion of the solid electrolyte plate 11; the terminal connection portion 23 has been omitted from the showing in FIG. 1, for clarity of illustration; the measuring electrode 15 is connected over conductive track 20 with the terminal connection 19. The protective electrode 18 is connected with the return line of the heater element 16 at the terminal end portion or connection region 21 thereof. The positive terminal of the heater element 16 is connected at the connection region 22—see FIGS. 1 and 3. As clearly apparent from FIGS. 1 and 2, the heater element 16 is physically above the protective or shielding electrode 18, although FIG. 3 shows the element side-by-side, for ease of illustration.

If desired, the flat surface 12 of the solid electrolyte plate 11 also may have a resistance heating element 16, including an electrical insulation layer, and a shielding electrode applied thereto. If this arrangement is selected, the positive terminal of the heater element on side 12 is to be connected with the terminal 22 in the terminal region of the plate; the return line of the heater element, as well as the protective electrode, is to be connected with the connection 21.

A similar arrangement of the resistance heating element 16 and of the electrical insulation layer 17 is suitable if both the measuring electrode 15 and the reference electrode 13 are located on the same surface of the electrolyte body, for example either surface 12 or 14. If such an arrangement is selected, the solid electrolyte plate need not be self-supporting, but the electrolyte element 11 may be formed by a thin solid electrolyte layer which is applied to an electrical insulator, such as a ceramic plate, an enamel metal plate or the like.

The resistance heating element arrangement, as described, can also be used with a sensor which operates in the current-limiting, or polarographic mode. If so, the two electrodes 13,15 should have a d.c. source connected thereto. Such a sensor described, for example, in the referenced patent 4,294,679, generates a measuring signal in which the output is proportional to the oxygen content of the gas to which the sensor is exposed. When utilizing the sensor construction for operation with a sensor operating in the polarographic mode, a diffusion barrier to control the migration of oxygen molecules to the measuring electrode is preferably provided; the diffusion barrier may be formed as a porous cover layer with predetermined diffusion characteristics or as narrow ducts through a ceramic body or the like.

The system effectively prevents leakage currents from adulterating the measuring output signals derived from the electrodes. The protective electrode 18 forms a shield on the electrically insulating layer 17 with respect to the resistance heating element 16 to prevent leakage currents. Additionally, upon connecting the sensor, for example in an automatic control system, the time until measuring signals suitable for control purposes are obtained is reduced.

Additional safety with respect to avoidance of leakage currents which flow from the resistance element 16 to the measuring electrode 15 and/or the reference electrode 13 can be obtained by applying an additional electrically insulating layer between the solid electrolyte plate 11 and the protective or shielding electrode 18. Such additional insulating layer can be similar to, or identical to, the electrically insulating layer 17, both with respect to substance as well as with respect to size and thickness.

FIG. 4 illustrates, in cross-section, a portion of a tubular solid electrolyte sensor forming a closed tube, the outside of which is exposed to the gas to be sensed or tested. The carrier of the sensor 24 is the solid electrolyte tube 25, described, for example, in U.S. Pat. No. 4,219,399. The solid electrolyte tube 25 is closed off at the bottom by a closed bottom wall, not shown. Such a solid electrolyte tube 25, which can be exposed, for example, directly to exhaust gases from an internal combustion engine, may have a outer diameter of about 8 mm, and a wall thickness of about 0.8 mm. It can be made of the same material as the solid electrolyte in plate form, that is, element 11 of FIGS. 1 and 2. At the terminal end, it is surrounded by a metallic housing, as described in the referenced patent 4,219,399. Such a sensor element 24 has a reference electrode 27 at the inner surface thereof, made of a porous platinum-type metal, or platinum, or platinum metal alloy. Preferably it leads down to the bottom closed end of the solid electrolyte tube 25, and has a thickness of about 7 $\mu$m. It can be applied by printing on the solid electrolyte tube inner surface 26, and is exposed to air, forming the gas of known oxygen content. Air is not the only substance, however, and mixtures of suitable metals and their metal oxides, such as, for example, nickel/nickel oxide may also be used within the solid electrolyte tube. The reference electrode 27 is preferably constructed in form of a strip and terminates in the region of the open end portion of the solid electrolyte tube 25 at the connecting end thereof.

The outer surface 28 of the solid electrolyte tube has a measuring or sensing electrode 29 applied thereto by any suitable process, such as printing, spraying, vapor deposition, or the like. Preferably, it is also made of a porous platinum, platinum-based alloy, platinum metal or the like, with a thickness of about 15 $\mu$m. The terminal region is connected to the open portion of the solid electrolyte tube. As in the embodiment of FIGS. 1 and 2, a porous protective covering applied to the measuring electrode 25 has been omitted from the drawing for simplicity. Such a covering is shown, for example, in U.S. Pat. No. 3,978,006, Topp et al., assigned to the assignee of the present application.

The sensor 24, like the sensor 10 of FIGS. 1 and 2, can operate either in the potentiometric, or polarographic mode, depending on its external connection and, if suitable for polarographic application, an oxygen molecule diffusion control layer or barrier is applied over the measuring electrode 29, as described above.

Sensor elements 24 may have a layer-like resistance heater 30 applied thereto. A first electrical insulation layer 31 is provided to separate the heater from the sensing electrode 29. The electrical insulation layer 31 is made wider than the resistance heating element 30. The thickness and material may be similar to the electrical insulation layer 17 of the sensor element 10. The resistance heater 16, likewise, can be similar to that described in connection with sensor 10. It is provided with a terminal connection region adjacent the open end portion of the solid electrolyte tube 25.

In accordance with the present invention, a second electrical insulation layer 32 is applied beneath the first electrical insulation layer 31 corresponding thereto in thickness and material, and located between the measuring electrode 29 and the solid electrolyte body 25. Preferably, however, the insulation layer 32 is somewhat wider than the first electrical insulation layer 31—see FIG. 4.

In this arrangement, the sensing electrode 29 simultaneously forms the protective or shield electrode. This embodiment is simple to manufacture and thus preferred from a manufacturing technology point of view, particularly for sensor elements of the type of element 24. The measuring electrode 29, which also forms the protective electrode, is connected to the return line of the resistance heating element 30 and, as seen in the circuit connection of FIG. 5, is connected to a common terminal 33. The further terminals are formed on the terminal end portion of the solid electrolyte tube 25, that is, the terminal region 34 of the reference electrode 27 at the inside of the tube, and the positive terminal 35 of the resistance heater element 30. The resistance heater element 30 may be a looped strip of platinum metal, as described in connection with FIG. 1, extending from one open end portion over and around the closed end portion of the tube and at the other side, diammetrically opposite the first strip, on the tube.

The sensor element 24, thus, has only three terminal connections 33,34,35. The sensor element 10 of FIG. 1 has four connecting regions 19,23 and 21 and 22.

A separate protective electrode could be placed between the resistance heating element 30 and the reference electrode 27 in order to prevent leakage current from arising, rather than using the measuring electrode itself as a protective shield beneath the heater electrode, by applying a measuring electrode and a protective electrode at different regions of the outer surface 28 of the solid electrolyte tube and separating the layers electrically from each other. Such an arrangement would, then, in principle, correspond to the arrangement of the resistance heating element 16, electrical insulation layer 17 and protective electrode 18 on the solid electrolyte 11 of the sensor element 10.

The heated sensor element 24 can be connected to a utilization circuit similar to an unheated sensor element and does not require high resistance separation between the heater network or heater circuit and the voltage supply of the evaluation circuit.

Various different types of solid electrolyte sensors may be used; rather than using a solid electrolyte sensor as described in the aforementioned patents and shown, in fragmentary representation in FIG. 4, solid electrolyte tubes may be used which do not have any bottom, or which have cross bores, so that the reference electrode and the sensing electrode both are exposed to the gas to be tested. In such a case, the reference electrode should be made of a material which is catalytically less active than that of the sensing electrode.

Different types of heater or resistance elements may be used for specific applications, for example the heaters may be in the form of wire-like resistance heater elements. This is particularly suitable for sensors having tubular solid electrolyte bodies.

Various changes and modifications may be made in features described in connection with any one of the embodiments and may be used with any of the others, within the scope of the inventive concept.

We claim:

1. Heated electrochemical sensor with internal shielding, to provide an electrical output representative of a predetermined component in a sample gas to which the sensor is exposed, particularly a combustion exhaust gas, especially from an internal combustion engine, having an oxygen ion conductive solid electrolyte body (11,25):

two porous electrode layers (13, 15; 27, 29) positioned on the body at spaced surface portions thereof;

a resistance heating element (16, 30) on the body. and an electrical supply connection (22, 35) and an electrical return connection (21, 33) to provide electrical current to the resistance heating element;

and an electrically insulating layer (17, 31) separating the resistance heating element from the solid electrolyte ion conductive body and supporting the resistance heating element thereon wherein, in accordance with the invention a layer-like shielding electrode (18, 29) is provided, positioned between the solid electrolyte body (11, 25) and the electrically insulating layer (17, 31) on which the resistance heating element is located and supported, and located beneath the resistance heating element.

2. Sensor according to claim 1 further including a second electrically insulating layer (32) located between the shielding electrode (18,29) and the solid electrolyte body (11,25).

3. Sensor according to claim 2 wherein the shielding electrode (29) and one of the porous electrode layers (29) are in electrical connection with each other.

4. Sensor according to claim 3 wherein the shielding electrode, and one of the porous electrode layers (29) form a continuous electrically conductive layer on the solid electrolyte body, the continuous layer acting as a porous electrode where said layer is in contact with the oxygen ion conductive solid electrolyte body and forming the shielding electrode in that region where said further electrically insulating layer (32) is interposed between said electrically conductive layer (29) and the ion conductive body (25).

* * * * *